US011376521B2

(12) United States Patent
Lucas

(10) Patent No.: US 11,376,521 B2
(45) Date of Patent: *Jul. 5, 2022

(54) EFFICIENT DISTILLATION OF ETHANOL

(71) Applicant: Lucas E3, L.C., Shawnee, KS (US)

(72) Inventor: Scott A. Lucas, De Soto, KS (US)

(73) Assignee: LucasE3, L.C., Shawnee, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/782,329

(22) Filed: Feb. 5, 2020

(65) Prior Publication Data

US 2020/0171404 A1 Jun. 4, 2020

Related U.S. Application Data

(63) Continuation-in-part of application No. 16/260,686, filed on Jan. 29, 2019.

(Continued)

(51) Int. Cl.

| C12F 3/10 | (2006.01) |
| B01D 3/00 | (2006.01) |
| B01D 3/14 | (2006.01) |
| B01D 21/26 | (2006.01) |
| B01D 53/18 | (2006.01) |
| B01D 53/34 | (2006.01) |
| B01D 53/76 | (2006.01) |
| B01D 53/44 | (2006.01) |
| B01D 53/02 | (2006.01) |

(Continued)

(52) U.S. Cl.
CPC ............... B01D 3/007 (2013.01); B01D 1/26 (2013.01); B01D 3/002 (2013.01); B01D 3/148 (2013.01); B01D 5/006 (2013.01); B01D 21/262 (2013.01); B01D 53/02 (2013.01); B01D 53/18 (2013.01); B01D 53/343 (2013.01); B01D 53/44 (2013.01); B01D 53/76 (2013.01); C07C 29/84 (2013.01); C12F 3/10 (2013.01); F26B 11/028 (2013.01); B01D 2253/116 (2013.01); B01D 2258/02 (2013.01); C07C 29/80 (2013.01)

(58) Field of Classification Search
CPC ........ B01D 3/001; B01D 3/002; B01D 3/003; B01D 3/004; B01D 3/005; C12M 47/10; C12M 47/14; C12M 47/18; C12F 3/06; C12F 3/08; C12F 3/10; C12H 6/02; C10G 2300/1014

See application file for complete search history.

(56) References Cited

U.S. PATENT DOCUMENTS 2,958,142 A 11/1960 Kershaw et al.
3,363,340 A 1/1968 McKinley
(Continued)

FOREIGN PATENT DOCUMENTS

AU 2007303117 4/2008

OTHER PUBLICATIONS

Katzen, et al., "Ethanol Distillation: the Fundamentals", 1999, 270-273.

*Primary Examiner* — Jonathan Luke Pilcher
(74) *Attorney, Agent, or Firm* — Law Office of Mark Brown, LLC; Mark E. Brown

(57) ABSTRACT

Systems and methods in accordance with the present invention provide for the efficient distillation of ethanol in an ethanol plant including a beer column. Heat is captured in the distillation process and utilized to drive operations in the ethanol plant.

1 Claim, 1 Drawing Sheet

Related U.S. Application Data

(60) Provisional application No. 62/623,459, filed on Jan. 29, 2018.

(51) Int. Cl.
    *B01D 5/00*          (2006.01)
    *B01D 1/26*          (2006.01)
    *C07C 29/84*        (2006.01)
    *F26B 11/02*        (2006.01)
    *C07C 29/80*        (2006.01)

(56) References Cited

U.S. PATENT DOCUMENTS

| | | |
|---|---|---|
| 3,673,705 A | 7/1972 | Wright et al. |
| 4,309,254 A | 1/1982 | Dahlstrom |
| 5,178,543 A | 1/1993 | Semans et al. |
| 5,354,203 A | 10/1994 | Kotch et al. |
| 7,504,546 B2 | 3/2009 | Brown et al. |
| 7,867,365 B2 | 1/2011 | Brown |
| 7,988,580 B2 | 8/2011 | McCrary |
| 8,173,412 B2 | 5/2012 | Dale |
| 9,029,126 B2 | 5/2015 | Bleyer et al. |
| 9,308,489 B2 | 4/2016 | Brown et al. |
| 9,931,582 B2 | 4/2018 | Furlong |
| 2009/0171724 A1 | 7/2009 | Allin et al. |
| 2011/0315541 A1 | 12/2011 | Ku |
| 2014/0053829 A1 | 2/2014 | Lee |
| 2014/0238881 A1 | 8/2014 | Stuhlmann et al. |
| 2014/0343259 A1 | 11/2014 | Bleyer et al. |
| 2015/0041305 A1 | 2/2015 | Overheul et al. |
| 2015/0045594 A1* | 2/2015 | Overheul ................ C10G 3/42 585/240 |
| 2016/0279560 A1 | 9/2016 | Furlong |
| 2018/0290073 A1 | 10/2018 | Brown et al. |
| 2019/0233354 A1* | 8/2019 | Lucas .................... B01D 5/006 |
| 2020/0171404 A1 | 6/2020 | Lucas |

* cited by examiner

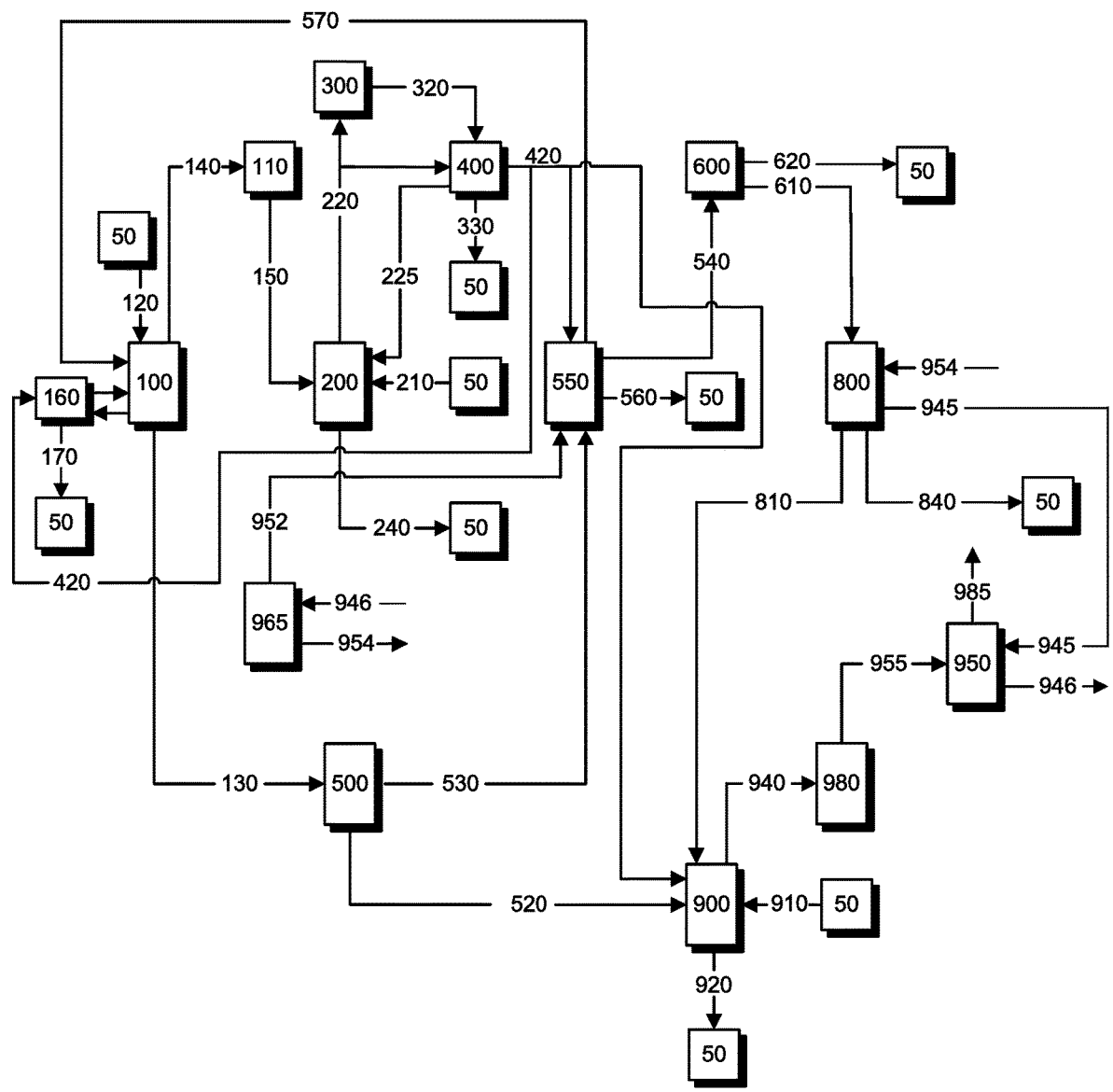

EFFICIENT DISTILLATION OF ETHANOL

CROSS-REFERENCE TO RELATED APPLICATION

This application is a Continuation-in-Part of and claims priority in U.S. patent application Ser. No. 16/260,686, filed Jan. 29, 2019, which claims priority in U.S. Provisional Patent Application No. 62/623,459, filed Jan. 29, 2018, all of which are incorporated herein by reference.

BACKGROUND OF THE INVENTION

1. Field of the Invention

The present invention provides systems and methods for improved distillation of ethanol in or in conjunction with an ethanol plant. Ethanol may be produced by fermenting grains, cellulosic material, or other organic matter to produce a beer containing a relatively low percentage of ethanol in a mixture with water, various dissolved solids, and other materials. The distillation process may separate the ethanol, which may be useful for fuel, industrial, or other uses, from the other components of the beer.

2. Description of the Related Art

Ethanol may be produced by fermenting grains, cellulosic material, or other organic matter to produce a beer containing a relatively low percentage of ethanol in a mixture with water, various dissolved solids, and other materials. The distillation process may separate the ethanol, which may be useful for fuel, industrial, or other uses, from the other components of the beer.

Distilling ethanol consumes significant quantities of energy resources, which represent a major operating expense for ethanol distillation plants. Efficient plant operation tends to reduce such operating expenses, thus lowering the costs of ethanol end products. Operating costs can be reduced and efficiencies can be increased by maximizing the effective use of energy inputs. For example, heat generated in one operation can be utilized for driving other operations. Current plant designs typically vent or discharge substantial quantities of heat to the atmosphere. Capturing such waste energy can improve efficiencies and reduce operating expenses.

The present invention addresses such ethanol distillation plant efficiency objectives by providing a method and system for capturing heat from dryer exhausts, and using such captured heat for driving ethanol distillation plant operations.

Heretofore there has not been available a system or method for distillation of ethanol with the advantages and features of the present invention.

SUMMARY OF THE INVENTION

In practicing an aspect of the present invention, a dryer exhaust heat subsystem captures heat from a dryer and further heats a warm water stream in a scrubber, which outputs hot water to the ethanol plant. In the practice of the method of the present invention, captured dryer exhaust heat increases overall ethanol plant efficiencies by reducing the net energy input required for driving plant operations.

BRIEF DESCRIPTION OF THE DRAWINGS

The drawings constitute a part of this specification and include exemplary embodiments of the present invention illustrating various objects and features thereof.

FIG. 1 is a schematic representation of an ethanol distillation system with a dryer exhaust heat capture subsystem for improving system performance, embodying an aspect of the present invention.

DETAILED DESCRIPTION OF THE PREFERRED EMBODIMENTS

I. Introduction and Environment

As required, detailed aspects of the present invention are disclosed herein, however, it is to be understood that the disclosed aspects are merely exemplary of the invention, which may be embodied in various forms. Therefore, specific structural and functional details disclosed herein are not to be interpreted as limiting, but merely as a basis for the claims and as a representative basis for teaching one skilled in the art how to variously employ the present invention in virtually any appropriately detailed structure.

Certain terminology will be used in the following description for convenience in reference only and will not be limiting. For example, up, down, front, back, right, and left refer to the invention as orientated in the view being referred to. The words "inwardly" and "outwardly" refer to directions toward and away from, respectively, the geometric center of the aspect being described and designated parts thereof. Said terminology will include the words specifically mentioned, derivatives thereof and words of similar meaning.

II. Preferred Embodiment

Systems and methods in accordance with the present invention may receive beer 120 from an ethanol plant 50. The beer 120 may contain between 12% wt and 15% wt ethanol and may be at a temperature between 140° F. and 160° F., although other percentages of ethanol content and other temperatures are possible in accordance with the present invention.

The beer 120 may be fed to the first distillation column, referred to as beer column 100. Beer column 100 may be run at a temperature between 150° F. and 170° F. at the bottom of the column 100. Beer column 100 may be driven by energy sources derived from integration with other components and systems of the plant 50. For example, the main energy source for beer column 100 may come from vapors 570 from the fourth effect of the main evaporators 550. An additional source of heat for beer column 100 may be from a reboiler 160 which condenses some of the steam vapors 420 from the vapor condensing system 400, producing a condensate stream 170, a portion of which can be returned to the ethanol plant 50 for reuse.

The stripped beer column bottoms 130 from the bottom of the beer column 100 may be sent to a centrifuge process 500 for further processing. The ethanol-rich vapors 140 produced by the beer column 100 may be condensed using a condenser 110. Condenser 110 may be cooled using cooling tower water. Condenser 110 may be run at a very low pressure of between 0.5 psia and 4 psia.

Ethanol-laden condensate 150 produced by the condenser 110 may be pumped to a rectifier system 200 where the ethanol may be purified to 190 proof ethanol vapor 220, for example, using either one or two columns that may be run in series. Steam 210 may be used to add heat to the rectifier system 200. The column(s) of rectifier system 200 may be operated at high pressure, such as between 50 psig and 70 psig, with the 190 proof vapors 220 from the column may be split between feeding the dehydration system 300, which may consist of molecular sieves or membrane technology, and being directly condensed using the vapor condensing system 400. The condensate 225 from the vapors that are directly fed to the vapor condensing system 400 are collected and sent back to the rectifier 200 as reflux.

Water may be removed from the 190 proof vapors 220 in the dehydration system 300. Dehydrated vapors 320, which will be at 200 proof, may be received from the dehydration system 300 and may be condensed using a vapor condensing system 400. The condensed 200 proof product 330 may be sent to the tank farm at the ethanol plant 50 for storage and load out.

The vapor condensing system 400 may be used to integrate the heat from the 190 proof vapors 220 directly received from the rectifier 200 and the 200 proof vapors 320 from the dehydration system 300 with other sections of the plant. The vapor condensing system 400 may condense the vapors and boil steam condensate to produce steam vapors 420. The steam vapors 420 may be used to drive the first effect of the main evaporators 550 and evaporation of water at the rotary dryer 900. The water phase 240 pulled from the bottom of the rectifier system 200 may be returned to the ethanol plant 50 for reuse.

The bottom stream 130 from the beer column 100 may first be sent to a centrifuge process 500 that may separate out most of the suspended solids into a solids cake 520. The solids cake 520 may be between 30% wt and 40% wt solids. The resultant low solids centrate 530 may be sent to the main evaporators 550 to produce a syrup product 540 and evaporator condensate 560, which may be returned to the ethanol plant 50 for reuse.

The syrup product 540 may be between 25% wt solids and 34% wt solids and may be sent to the corn oil extraction system 600 where product corn oil 620 may be removed from the syrup to produce a de-oiled syrup product 610. Product corn oil 620 may be sent to the ethanol plant 50 for storage and load out.

The de-oiled syrup 610 may then be sent to the finish evaporators 800 where the syrup may be further concentrated to finished syrup 810 having between 38% wt and 74% wt solids. The evaporator condensate 840 from the finish evaporators 800 may be returned to the ethanol plant 50 for reuse.

The solids cake 520 from the centrifuge system 500 may be mixed with the finished syrup 810 from the finish evaporators 800 and then may be sent to a rotary dryer 900 and heated using steam vapors 420 from the vapor condensing system 400 to produce a distillers dried grains with solubles (DDGS) product 920. This DDGS product 920 may be between 8% wt and 12% wt moisture and may be sent to another area of the ethanol plant 50 for storage and load out.

The distillers dried grains (DDG) dryer exhaust 940 may be diverted to a regenerative thermal oxidizer (RTO) 980 which removes organic impurities from the exhaust gas before the treated gas 955 is fed to a scrubber 950 where the dryer exhaust 940 may be contacted counter its current with a warm water stream 945. This water stream may be heated to between 185° F. and 205° F. and may leave the bottom of the scrubber 950 as supply hot water 946. The exhaust gas 955 may be vented from the top of the scrubber 950 to the atmosphere.

The supply hot water 946 produced by the scrubber 950 may be pumped to a hot water flash tank 965 located next to the main evaporators 550 where the water stream may be flashed to sending vapors 952 to the third effect of four effects, of the main evaporators 550. The hot water return 954 leaving the bottom of the hot water flash tank 965 may then be pumped to the finish evaporators 800, where the hot water may be used to transfer heat to the evaporator to vaporize water from the de-oiled syrup 610 to produce finished syrup 810. The hot water return 954 may be cooled, producing warm water return 945 that may be sent back to the scrubber 950. The evaporator condensate 840 from the finishing evaporators 800 may be returned to the ethanol plant 50 for reuse.

It is to be understood that the invention can be embodied in various forms and is not to be limited to the examples specifically discussed above. The range of components and configurations which can be utilized in the practice of the present invention is virtually unlimited.

Having thus described the invention, what is claimed as new and desired to be secured by Letters Patent is:

1. A heat capture system for an ethanol distillation plant including a beer column driven by energy sources from the plant, which system includes:
   a distillers dried grains (DDG) dryer with an exhaust;
   a regenerative thermal oxidizer (RTO) receiving DDG dryer exhaust and configured for removing organic impurities therefrom to produce treated gas;
   a scrubber vented to the atmosphere and configured for receiving said treated gas;
   said scrubber further configured for contacting a warm water return from said plant, heating said warm water return and supplying hot water to said plant;
      wherein the DDG dryer is configured for producing the DDG dryer exhaust to said RTO;
   said DDG dryer receiving steam from said ethanol plant;
   a finish evaporator configured for receiving said warm water stream and feeding same to said scrubber;
   said beer column is configured for receiving beer from said ethanol plant;
   a reboiler connected to said beer column and configured for providing steam to said ethanol plant;
   a centrifuge connected to said beer column and configured for receiving a bottom stream from said beer column and providing said solids cake to said DDG dryer;
   a condenser connected to the beer column;
   rectifier system connected to a condenser;
   said rectifier system configured for splitting ethanol vapors between a molecular sieve system and a vapor condensing system;
   said vapor condensing system is configured to condense vapors and boil steam condensate to produce steam vapors;
   a first effect main evaporator configured for being driven with said steam vapors;
   a reboiler connected to said beer column and configured for being driven with said steam vapors;
   the beer column configured for receiving a hot water stream from said plant, and returning warm water to said scrubber;
   an evaporator configured for receiving low solids centrate from said centrifuge process; and
   said evaporator configured for supplying vapors to said beer column.

* * * * *